United States Patent [19]
Roffman et al.

[11] Patent Number: 5,796,462
[45] Date of Patent: *Aug. 18, 1998

[54] ASPHERIC TORIC LENS DESIGNS

[75] Inventors: Jeffrey H. Roffman; Edgar V. Menezes, both of Jacksonville, Fla.

[73] Assignee: Johnson & Johnson Vision Products, Inc., Jacksonville, Fla.

[*] Notice: The term of this patent shall not extend beyond the expiration date of Pat. No. 5,652,638.

[21] Appl. No.: 708,362

[22] Filed: Sep. 4, 1996

Related U.S. Application Data

[63] Continuation of Ser. No. 433,742, May 4, 1995, abandoned.
[51] Int. Cl.⁶ .................... G02C 7/04; G02C 7/02; A61F 2/16
[52] U.S. Cl. .................... 351/161; 351/160 H; 351/176; 623/6
[58] Field of Search .................... 351/159, 160 R, 351/160 H, 161, 168, 177, 176; 623/6

[56] References Cited

U.S. PATENT DOCUMENTS

| | | | |
|---|---|---|---|
| 3,960,442 | 6/1976 | Davis et al. | 351/176 |
| 4,095,878 | 6/1978 | Fonti | 351/161 |
| 5,050,981 | 9/1991 | Roffman | 351/177 |
| 5,125,729 | 6/1992 | Mercure | 351/161 |
| 5,406,341 | 4/1995 | Blum et al. | 351/160 R |
| 5,455,641 | 10/1995 | Hahne et al. | 351/160 H |
| 5,570,143 | 10/1996 | Newman | 351/160 R |

FOREIGN PATENT DOCUMENTS

WO 93/03409  2/1993  WIPO.

*Primary Examiner*—Georgia V. Epps
*Assistant Examiner*—Jordan M. Schwartz

[57] ABSTRACT

Aspheric toric lens designs are disclosed which reduce the number of cylindrical axis locations required for stock keeping units in inventory by aspherizing the toric surface thereof. The present invention pertains to ophthalmic lenses, and in particular to contact lenses such as soft hydrogel contact lenses, particularly designed to fit astigmatic patients who are either non-presbyopic or presbyopic. One of the front and back surfaces of the aspheric toric lens defines a spherical surface corresponding at least to the patient's basic distance prescription Rx. The other of the front and back surfaces defines an aspheric toric curve, wherein the toric surface is constructed with aspheric radii, such that the aspheric curve desensitizes axial misalignment of the toric curve by providing an enhanced depth-of-focus. When the aspheric toric surface is on the back surface of the lens, the spherical curve on the front surface of the lens can comprise a single spherical curve corresponding to the patient's basic distance prescription Rx. When the aspheric toric curve is on the front surface of the lens, the spherical curve on the back surface of the lens can comprise a multifocus concentric annular ring spherical surface design.

18 Claims, 2 Drawing Sheets

ASPHERIC TORIC LENS DESIGNS

This is a continuation of application Ser. No. 08/433,742, filed May 4, 1995 now abandoned.

BACKGROUND OF THE INVENTION

1. Field of the Invention

The present invention relates generally to aspheric toric lens designs. More particularly, the subject invention pertains to aspheric toric lens designs which reduce the number of cylindrical axis placement orientations required for stock keeping units maintained in inventory by aspherizing the toric surface thereof. The present invention relates to aspheric toric lens designs which reduce the number of stock keeping units maintained in inventory which are required to fit astigmatic patients who are either non-presbyopic or presbyopic.

2. Discussion of the Prior Art

The present invention pertains to ophthalmic lenses, and in particular to contact lenses such as soft hydrogel contact lenses, and intraocular lenses, having more than one optical power or focal length, and in particular to toric lenses.

Current toric lens designs use spherical radii to construct the toric surface. The prior art toric lens designs correct astigmatism, but require many different cylindrical axis orientations for different stock keeping units maintained in inventory (the total number of different possible prescriptions maintained in inventory), which disadvantageously results in a very large number of stock keeping units maintained in inventory.

In conventional toric lens designs, a single toric surface is placed in the optical portion of either the front or back surface of the lens. The other surface of the lens is typically spherical and corresponds to the basic spherical distance correction prescription of the patient. The axes of the toric lens are usually stabilized in relation to the patient's corneal axes through the use of either prism ballast/slab-off or double slab-off features placed on the front surface of the lens.

Conventional toric lens designs require a large number of stock keeping units in inventory in order to fit the astigmatic patient base. For example, current Frequent Replacement Toric lens products for non-presbyopes are available in 800 stock keeping units (40 spherical powers×2 cylindrical powers×10 cylindrical axis orientations). In order to provide such lenses for presbyopes, the stock keeping units have to be multiplied by the number of add powers. Such a large number of stock keeping units is uneconomical to produce and maintain in inventory, particularly in a disposable modality product. The large number of stock keeping units arises primarily from the need to provide multiple cylindrical axis orientations, cylindrical powers and add powers.

In an attempt to reduce the required number of cylindrical axis placements in stock keeping units, Australian Patent Application WO 93/03409 combines aspheric surfaces with toric surfaces to accommodate toric axial misalignment through the increased depth-of-focus provided by aspheres. The use of an aspheric surface enhances the depth-of-field of toric lenses and minimizes the effect of rotational misalignment of the toric lenses. Complex optics such as diffraction optics using echelets or birefringence optics are also disclosed by this published patent application. This patent application does not address the need for or enable the combination of a toric lens product having low number of stock keeping units, with a multifocal surface to correct presbyopic astigmatism, which is a principal advantage of the present invention thereover.

It is well known that as an individual ages, the eye is less able to accommodate, i.e. bend the natural lens in the eye, in order to focus on objects that are relatively near to the observer. This condition is referred to as presbyopia, and presbyopes have in the past relied upon spectacles or other lenses having a number of different regions with different optical powers to which the wearer can shift his vision in order to find the appropriate optical power for the object or objects upon which the observer wishes to focus.

Patent application Ser. No. 07/988,088, now U.S. Pat. No. 5,448,312, issued Sep. 5, 1995, entitled PUPIL TUNED MULTIFOCAL OPHTHALMIC LENS, discloses a multifocal concentric ophthalmic lens for presbyopic patients constructed with three general annular lens portions in a multifocal design. A central circular portion of the lens has only the patient's distance corrective power, and is surrounded by a first inner annular portion, which can consist of multiple annular rings having an inner radial portion which enhances the patient's near focal power encircled by radial portions of variable cumulative amounts of distance and near optical power focal correction for the patient. This is surrounded by a second outer annular portion, which can also consist of one or more annular rings having additional distance focal power near the periphery of the optical surface area of the ophthalmic lens. Each annular ring has either a near or distance optical power and works in combination with other lens portions to yield the desired focal ratio in that portion of the lens.

SUMMARY OF THE INVENTION

Accordingly, it is a primary object of the present invention to provide aspheric toric lens designs which reduce the number of cylindrical axis locations required for stock keeping units in inventory by aspherizing the toric surface thereof. The present invention pertains to ophthalmic lenses, and in particular to contact lenses such as soft hydrogel contact lenses, particularly designed to fit astigmatic patients who are either non-presbyopic or presbyopic.

A further object of the subject invention is the provision of toric contact lens designs in which the toric surface is constructed with the use of aspheric radii instead of spherical radii as in the prior art.

In accordance with the teachings herein, the present invention provides an aspheric toric lens for astigmatic patients wherein one of the front and back surfaces defines a spherical surface. The other of the front and back surfaces defines an aspheric toric curve, wherein the combination of the spherical surface and the toric curve corresponds at least to the patient's basic distance prescription, and wherein the toric surface is constructed with aspheric radii, such that the aspheric curve desensitizes axial misalignment of the toric curve by providing an enhanced depth-of-focus.

In greater detail, the aspheric curve can comprise an elliptical curve, or a parabolic curve, or a hyperbolic curve. The aspheric toric surface can be on either the back or front surface of the lens. The spherical curve can comprise a single spherical curve, or a multifocus concentric annular ring spherical surface design having a central circular spherical disc corresponding to the patient's basic spherical distance prescription, at least one annular spherical ring corresponding to the patient's basic spherical distance prescription, and at least one annular spherical ring corresponding to the patient's spherical near prescription, wherein the multifocus concentric annular ring design corrects for presbyopia and also enhances the depth-of-focus of the toric curve. The lens can comprise a contact lens, such as a soft hydrogel, or an intraocular lens.

BRIEF DESCRIPTION OF THE DRAWINGS

The foregoing objects and advantages of the present invention for aspheric toric lens designs may be more readily understood by one skilled in the art with reference being had to the following detailed description of several preferred embodiments thereof, taken in conjunction with the accompanying drawings wherein like elements are designated by identical reference numerals throughout the several views, and in which.

DETAILED DESCRIPTION OF THE DRAWINGS

The present invention relates to aspheric toric lens designs which aspherize the toric surface of the lens in a manner which allows the aspheric form to eliminate the requirement for multiple cylindrical axis orientations, cylindrical powers and add powers.

Figure 1:
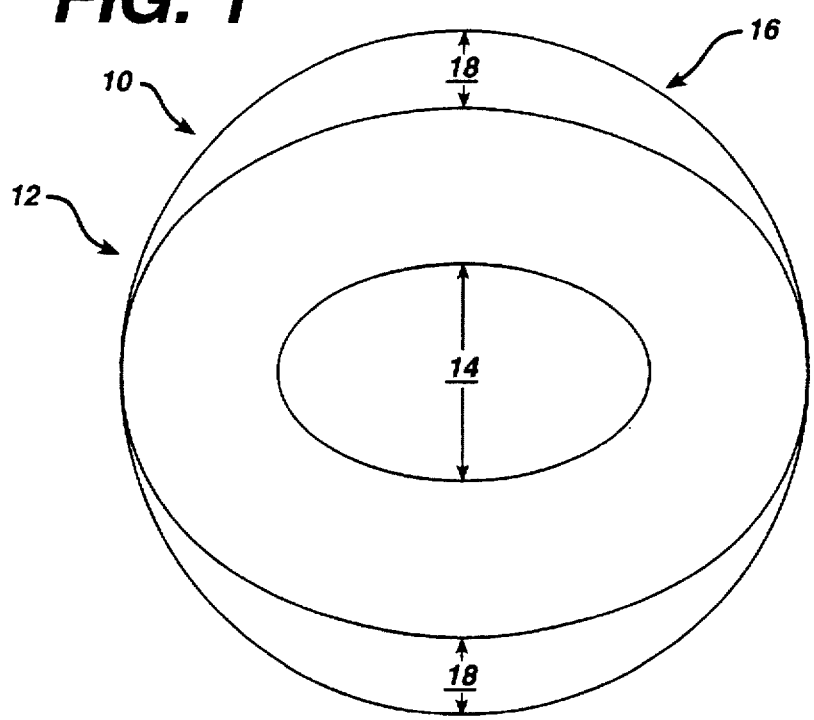
FIG. 1 illustrates a plan view of the back surface of a first embodiment of an aspheric toric lens design pursuant to the present invention which comprises a back surface as illustrated consisting of an aspherical toric surface in a 180 degree axial position, and a spherical front surface corresponding to the patient's basic spherical prescription.

FIG. 1 illustrates a plan view of the back surface of a first embodiment of an aspheric toric lens design 10 pursuant to the present invention which comprises a back surface 12 as illustrated consisting of an aspherical toric surface 14 in an exemplary 180 degree axis position, and a spherical front surface 16, not illustrated in detail, corresponding to the patient's basic spherical prescription.

The toric surface 14 can be described by the following general aspheric equation, which can be utilized to calculate each of the prime meridians of the lens:

$$X = \frac{cy^2}{1 + 1\sqrt{-c^2y^2(k+1)}}$$

where c is the apical vertex curvature, y is the distance from the axis (semichord), k is the conic constant where k=0= sphere, k=−1=parabola, −1<k<0=ellipse, +k,−1=hyperbola. A double slab-off feature 18 is incorporated to stabilize the axes of the aspheric toric curve on the back surface of the lens in either a 90 degree or 180 degree axis position. In an alternative embodiment, the aspheric toric surface can be placed on the anterior or front side of the lens and the spherical curve placed on the posterior or back side of the lens.

The form of the asphere which is superimposed on the toric surface can be designed based upon eliminating lens and ocular aberrations or by optimizing the retinal image quality (MTF). The aspheric toric surface is constructed with the use of aspheric radii instead of spherical radii as in the prior art, and provides a sufficient depth-of-focus effect to allow cylindrical axis misalignment of up to + or −20 degrees from the reference 90 degree or 180 degree positions, and can correct for astigmatism up to −2.00 D with a lower cylindrical power (e.g. −1.50 D).

Figure 2:
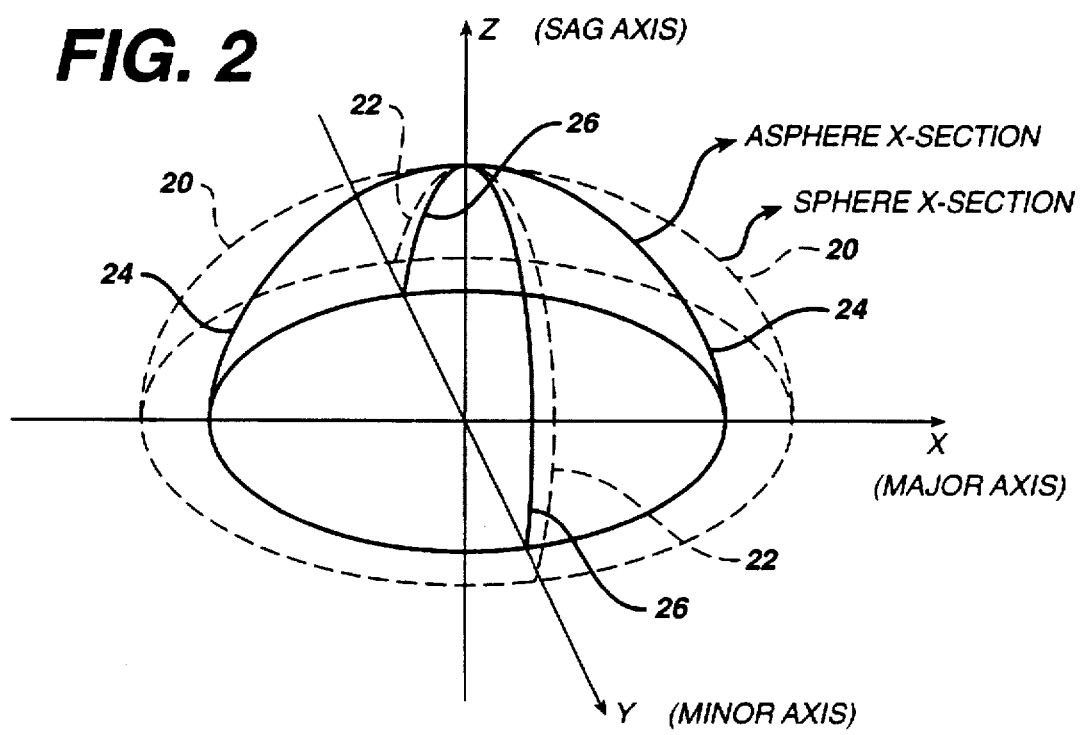
FIG. 2 illustrates one potential effect of aspherizing the toric surface, and illustrates in dashed lines a toric surface with a spheric cross-section at the major and minor axes of the toric surface, and also illustrates in solid lines a toric surface with an aspheric cross-section at the major and minor axes of the toric surface.

FIG. 2 illustrates the effect of aspherizing the toric surface, and illustrates in dashed line 20 a toric surface with a spheric cross-section at the major axis, and in dashed line 22 a toric surface with a spheric cross-section at the minor axis of the toric surface. FIG. 2 also illustrates in solid line 24 a toric surface with an aspheric cross-section at the major axis and illustrates in solid line 26 a toric surface with an aspheric cross-section at the minor axis of the toric surface. For negative eccentricity values, the effective cylinder will decrease from the center of the lens toward the periphery of the optic zone since more plus is added as a function of radial distance.

Figure 3:
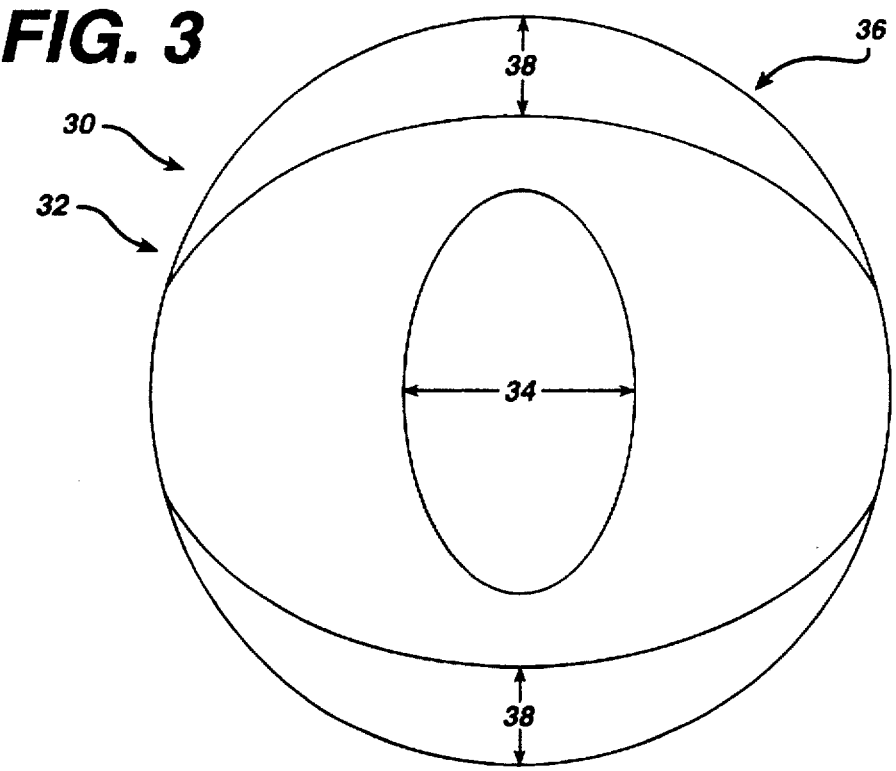
FIG. 3 illustrates a plan view of the front surface of a second embodiment of an aspheric toric lens design for presbyopic astigmatic patients pursuant to the present invention which comprises a front surface for the astigmatic correction consisting of an aspherical toric surface in a 90 degree axial position, and a back surface for the presbyopic correction which comprises a multifocus concentric annular ring design corresponding to the patient's basic spherical distance and near correction prescription.

FIG. 3 illustrates a plan view of the front surface of a second embodiment of an aspheric toric lens design 30 for presbyopic astigmatic patients pursuant to the present invention which comprises a front surface 32 for the astigmatic correction which consists of an aspherical toric surface 34 in an exemplary 90 degree axis position, and a back surface 36 for the presbyopic correction which comprises a multifocus concentric annular ring design corresponding to the patient's basic spherical distance and near correction prescription. In the second embodiment, in order to correct presbyopia in the astigmatic population, the aspherical toric surface is placed on the anterior or front surface of the lens and a multifocus concentric annular ring is placed on the posterior or back surface. Again, the depth-of-focus effect from the asphere will correct up to 2.00 D add with a lower add power (e.g. 1.50 D).

Figure 4:
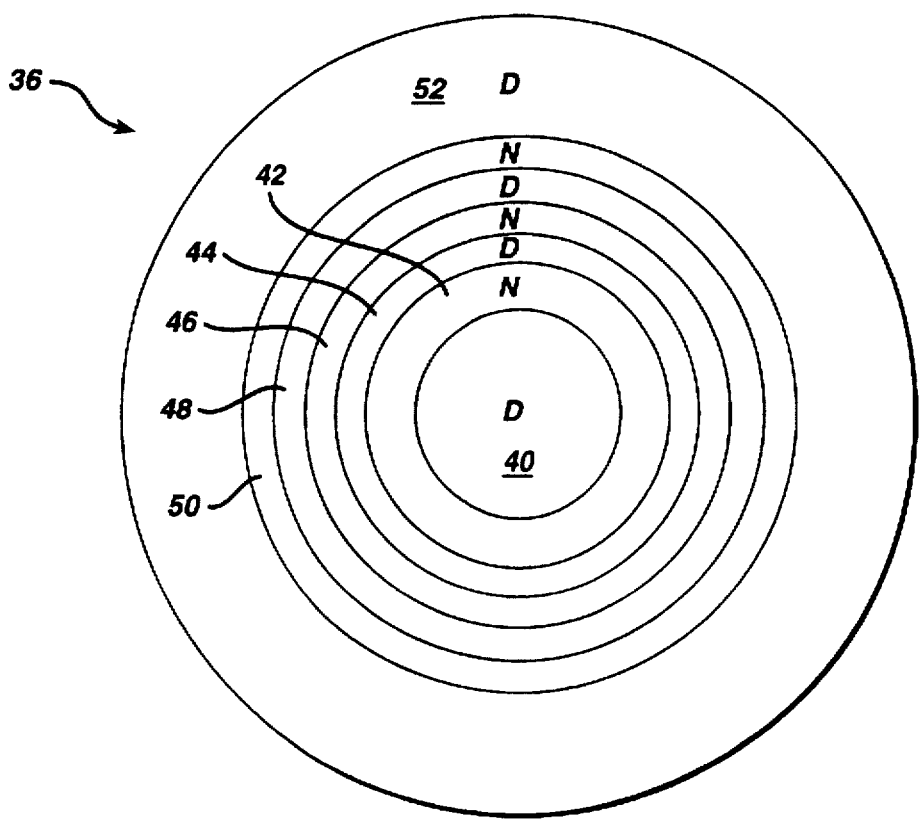
FIG. 4 illustrates a plan view of the back surface of the second embodiment of FIG. 3, which provides the presbyopic correction and comprises a multifocus concentric annular ring design corresponding to the patient's basic spherical distance and near correction prescription.

FIG. 4 illustrates one exemplary embodiment of a multifocal concentric ring back surface 36, and shows just the optic zone of the lens, which would correspond in size to the size of the toric surface 34, and is normally surrounded by a lenticular (nonoptical) portion of the lens which is not shown in FIG. 4. The multifocal, concentric ring back surface provides the presbyopic correction, and includes a central area 40 of the lens which is a circular disc containing the basic prescribed spherical distance power, and is surrounded by a plurality of alternating spherical near power and spherical distance power annular rings 42, 44, 46, 48, 50 and 52. The central circular portion 40 of the lens has only the patient's distance corrective power to provide distance corrective power under high illumination conditions (when the pupil is contracted). This is surrounded by a first relatively wide annular ring 42 to provide an enhanced contribution of near vision optical power to provide an approximately equal amount of near and distance focal length images under intermediate light conditions. This is surrounded by alternating distance and near annular rings 44, 46, 48 and 50, providing substantially equal cumulative amounts of distance and near optical power focal correction for the patient. This is surrounded by an outer annular ring 52 having additional distance focal power near the periphery of the optical surface area of the ophthalmic lens to provide enhanced distance optical power under low illumination conditions. A typical contact lens is usually constructed with a non-optical lenticular area (not shown) outside the optical surface for a total diameter of approximately 14 mm.

The present invention allows a significant reduction in the number of stock keeping units in inventory required to fit the same population of astigmatic presbyopes and non-presbyopes as shown by the TABLE below:

TABLE

| Conventional Torics: | |
| --- | --- |
| Spheres (−6D to +4D, in 0.25D steps) = | 40 |
| Cylinders (−1.25D, −2.00D) = | 2 |
| Axes (90, 180 +/− 20 in 10 deg. steps) = | 10 |
| Adds (none, 1.25D, 2.00D) = | 3 |
| TOTAL = | 2400 |
| The Present Invention: | |
| Spheres (−6D to +4D, in 0.25D steps) = | 40 |
| Cylinders (−1.50D) = | 1 |
| Axes (90, 180) = | 2 |
| Adds (none, 1.50D) = | 2 |
| TOTAL = | 160 |

The present invention desensitizes the requirements of many cylindrical axis locations required for stock keeping units in inventory by aspherizing the toric surface thereof.

Different embodiments of aspheres for use in the present invention include all conic aspheres, including ellipses, parabolas, and hyperbolas. The aspheres can be arrived at by empirical trial and error or by the use of in vivo modulation transfer function (MTF) devices which can help in identifying and reducing aberrations. The result of this will be toric lenses with decreased requirements for a large number of stock keeping units in inventory and provide patients with improved visual acuity.

The present invention can start with aspheric toric lens designs, possibly combined with multifocal annular ring lens designs, as illustrated in FIGS. 1–4, and then use in vivo image quality analysis equipment, such as an aberroscope or MTF point spread apparatus, to evaluate, identify and quantify any residual aberrations of the lens in place on the patient's eye. These residual aberrations can then be reduced further by modifying the lens design, such as by modifying the aspherization of the lens to improve visual performance and acuity. Thus, the present invention provides an improvement in the performance of designs for spherical ametropia, presbyopia, or astigmatism which is accomplished by a reduction of aberrations of the combination of the lens and the eye system. The reduction in aberrations does not correct the ametropia by itself. First, a subject (or population) is fitted with a concentric lens, and then the subject (or population) is tested with an in vivo image quality device to determine residual aberrations with the lens in place on the eye. Next, the lens is redesigned to decrease the measured residual aberrations.

Obviously, many different embodiments of the present invention are possible, with alterations of the type of aspheric toric curve, or by the number of annular rings, the widths and arrangement of the annular rings, etc.

While several embodiments and variations of the present invention for a aspheric toric lens designs are described in detail herein, it should be apparent that the disclosure and teachings of the present invention will suggest many alternative designs to those skilled in the art.

What is claimed is:

1. An aspheric toric lens for astigmatic patients comprising:

a. said lens having a front surface and an opposite back surface;

b. one of the front and back surfaces defines a spherical surface;

c. the other of the front and back surfaces defines an aspheric toric surface comprising an aspheric toric curve constructed with aspheric radii, wherein the aspheric radii desensitize axial misalignment by providing an enhanced depth of focus, and wherein the spherical surface of the lens comprises a multifocus concentric annular ring spherical design having a central circular spherical disc corresponding to the patient's basic spherical distance prescription, and at least one annular spherical ring corresponding to the patient's basic spherical distance prescription, and at least one annular spherical ring corresponding to the patient's spherical near prescription, wherein the multifocus concentric annular ring design corrects for presbyopia and also enhances the depth-of-focus of the aspheric toric curve.

2. An aspheric toric lens for astigmatic patients as claimed in claim 1, wherein the aspheric toric curve comprises an elliptical curve.

3. An aspheric toric lens for astigmatic patients as claimed in claim 1, wherein the aspheric toric curve comprises a parabolic curve.

4. An aspheric toric lens for astigmatic patients as claimed in claim 1, wherein the aspheric toric curve comprises a hyperbolic curve.

5. An aspheric toric lens for astigmatic patients as claimed in claim 1, wherein the aspheric toric surface is the back surface of the lens.

6. An aspheric toric lens for astigmatic patients as claimed in claim 1, wherein the aspheric toric surface is the front surface of the lens.

7. An aspheric toric lens for astigmatic patients as claimed in claim 1, wherein the lens comprises a contact lens.

8. An aspheric toric lens for astigmatic patients as claimed in claim 7, wherein the contact lens comprises a soft hydrogel contact lens.

9. An aspheric toric lens for astigmatic patients as claimed in claim 1, wherein the lens comprises an intraocular lens.

10. The aspheric toric lens as claimed in claim 1, wherein said central circular spherical disc corresponding to the patient's basic spherical distance perscription is surrounded by a plurality of alternating spherical rings said spherical rings corresponding to the patient's basic distance and near prescriptions.

11. An aspheric toric lens for astigmatic patients comprising:

a. said lens having a front surface and an opposite back surface;

b. one of the front and back surfaces defines a multifocus concentric circular annular ring spherical surface;

c. the other of the front and back surfaces defines an aspheric toric surface comprising an aspheric toric curve constructed of aspheric radii, wherein the combination of the spherical surface and the aspheric toric curve corresponds at least to the patient's basic distance prescription, and wherein the aspheric radii desensitize axial misalignment of the aspheric toric curve by providing an enhanced depth-of-focus.

12. An aspheric toric lens for astigmatic patients as claimed in claim 11, wherein the aspheric toric curve comprises an elliptical curve.

13. An aspheric toric lens for astigmatic patients as claimed in claim 11, wherein the aspheric toric curve comprises a parabolic curve.

14. An aspheric toric lens for astigmatic patients as claimed in claim 11, wherein the aspheric toric curve comprises a hyperbolic curve.

15. An aspheric toric lens for astigmatic patients as claimed in claim 11, wherein the aspheric toric surface is the back surface of the lens.

16. An aspheric toric lens for astigmatic patients as claimed in claim 11, wherein the aspheric toric surface is the front surface of the lens.

17. An aspheric toric lens for astigmatic patients as claimed in claim 11, wherein the lens comprises a contact lens.

18. An aspheric toric lens for astigmatic patients as claimed in claim 11, wherein the lens comprises an intraocular lens.

* * * * *